United States Patent [19]

Portoghese

[11] 4,362,870

[45] Dec. 7, 1982

[54] SELECTIVE OPIOID RECEPTOR ALKYLATING AGENTS

[75] Inventor: Philip S. Portoghese, St. Paul, Minn.

[73] Assignee: Regents of the University of Minnesota, Minneapolis, Minn.

[21] Appl. No.: 245,052

[22] Filed: Mar. 19, 1981

Related U.S. Application Data

[63] Continuation-in-part of Ser. No. 112,556, Jan. 16, 1980, abandoned.

[51] Int. Cl.$^3$ .................. C07D 489/08; A61K 31/485
[52] U.S. Cl. ..................................... 542/403; 546/44; 546/46; 424/260
[58] Field of Search ..................... 544/44, 46; 542/403

[56] References Cited

U.S. PATENT DOCUMENTS 3,332,950  7/1967  Blumberg et al. ............... 546/44 X
4,241,066 12/1980  Kobylecki et al. ................ 424/260
4,241,067 12/1980  Kobylecki et al. ................ 424/260

FOREIGN PATENT DOCUMENTS 2812580 10/1978 Fed. Rep. of Germany.

OTHER PUBLICATIONS

Jiang, et al. J. Med. Chem., 20(8), pp. 1100–1102 (1977).
Portoghese, et al., J. Med. Chem., 21, pp. 598–599 (1978).
Portoghese, et al., J. Med. Chem., 22(2), pp. 168–173 (1979).
Portoghese, et al., J. Med. Chem., 23(3), pp. 233–234 (03/80).
Caruso, et al., Science, 204, pp. 316–318 (04/20/79).

Primary Examiner—Donald G. Daus
Assistant Examiner—Diana G. Rivers
Attorney, Agent, or Firm—Burd, Bartz & Gutenkauf

[57] ABSTRACT

A selective opioid receptor, site-directed alkylating agent useful as a narcotic antagonist and non-addictive analgesic having the formula:

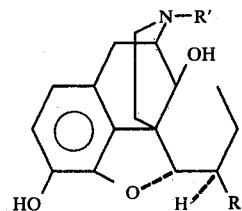

wherein R is a Michael acceptor, a haloacetamide or isothiocyanate and R' is cyclopropylmethyl, allyl or substituted allyl. The Michael acceptors may be acrylamides or esters:

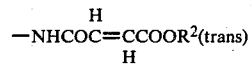

wherein $R^2$ is alkyl or aralkyl, and salts thereof. The preparation of the compounds is described, along with experiments involving the use of the compounds.

4 Claims, 2 Drawing Figures

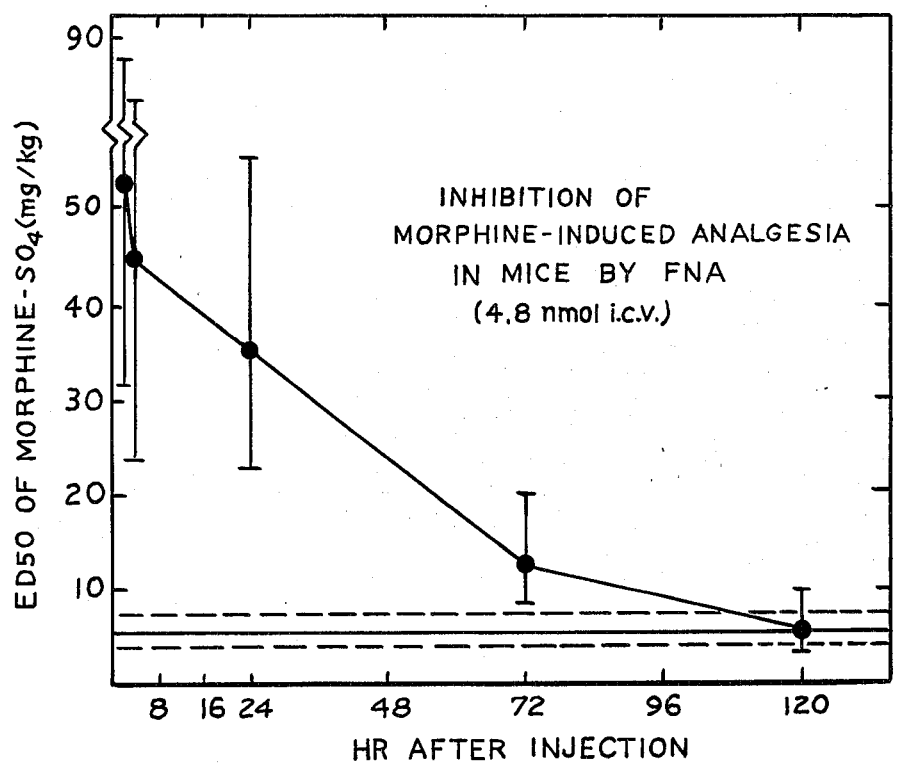
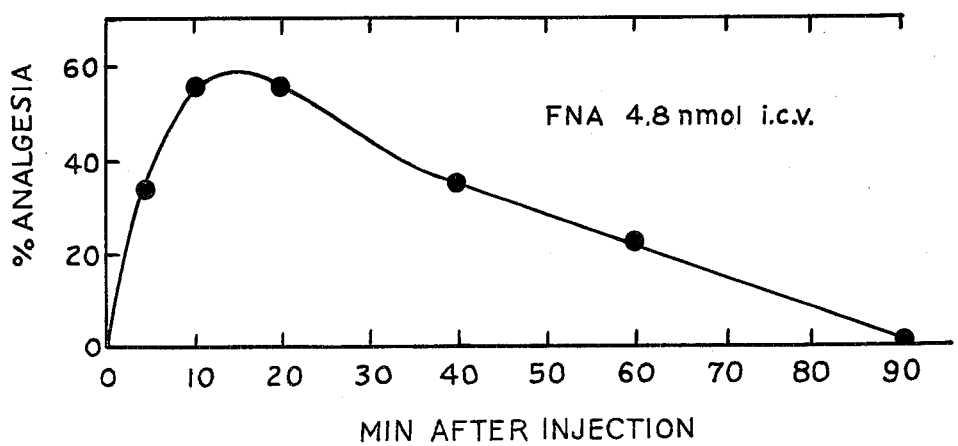

SELECTIVE OPIOID RECEPTOR ALKYLATING AGENTS

The Government has rights in this invention pursuant to Contracts DA 01533 and DA 00289 awarded by the National Institutes of Health.

This application is a continuation-in-part of application Ser. No. 112,556, filed Jan. 16, 1980 abandoned.

BACKGROUND OF THE INVENTION

1. Field of the Invention

This invention is directed to new and improved long-acting narcotic antagonists and non-addictive analgesics. More particularly, the invention is directed to opioid receptor site-directed alkylating agents, and to the method of synthesizing the same.

2. The Prior Art

Narcotic antagonists have received considerable attention over the past several years, particularly since the discovery of the endorphins. Besides being useful as prophylactic agents in the management of narcotic addiction and as nonaddictive analgesics, they have more recently been employed on an experimental basis in the treatment of mental illness. Additionally, the report that β-endorphin-induced stimulation of food intake is blocked by naloxone also suggests that narcotic antagonists might have potential as appetite suppressants. The action of enkephalin and enkephalin analogues as potent hypotensive agents also suggests that nonpeptide analogues might find use in the treatment of hypertension.

For these reasons, compounds with narcotic antagonist activity which specifically antagonize the actions of narcotics or of endogenous peptides (e.g., endorphins) might find application in the treatment of a variety of conditions. Also, properly modified agonists or mixed agonist-antagonists conceivably might give rise to new classes of anti-hypertensive agents and anti-obesity drugs.

With the accumulation of evidence which supports the concept of multiple opioid receptors and their classification into subtypes, it is becoming apparent that exogenously administered opioids mediate their manifold effects through several types of receptors.

Our approach to designing compounds that are selective and have prolonged activities is based upon the attachment of alkylating groups to ligands which are recognized by opioid receptors. The formation of a covalent bond with the receptor will enable the drug to remain in the receptor locus and thereby exert its effects for extended periods. Such drugs would not be subject to the normal disposition processes which ordinarily terminate their action.

An important feature in the design of such drugs takes into account the location of the nucleophile which forms the covalent bond with the reactive group. As the presence of the reactive moiety does not necessarily lead o covalent association after a drug-receptor complex is formed, it is apparent that the position of attachment of the alkylating group on to the pharmacophore is of critical importance. Thus, while there have been a number of attempts to design opioid receptor site-directed alkylating agents, only recently has this goal been successfully executed. This was demonstrated with the ultralong-acting narcotic antagonist, chlornaltrexamine (CNA) [Portoghese et al, *J. Med. Chem.*, 21, 598 (1978) and Portoghese et al, *J. Med. Chem.*, 22, 168 (1979)] and the irreversible agonist, chloroxymorphamine (COA) [Caruso et al, *Science,* 204, 316 (1979)]. These reports demonstrated the presence of a receptor nucleophile proximal to the alkylating group on the drugs.

Once the location of the receptor nucleophile is known, it should be possible to design much more selective compounds which would alkylate selected subclasses of opioid receptors. Presumably, this selectivity would be a consequence of differences in the nature and location of the nucleophiles in different receptors. The present invention is directed to compounds produced as the result of such an approach.

SUMMARY OF THE INVENTION

The invention resides in opioid receptor alkylating agents having the formula:

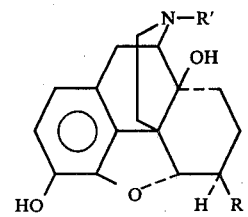

wherein R is a Michael acceptor, a haloacetamide or an isothiocyanate and R' is cyclopropylmethyl, allyl or substituted allyl. The Michael acceptors may be acrylamides or esters of the general formula:

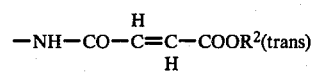

wherein $R^2$ is an alkyl or aralkyl group, and salts thereof. The latter compound is prepared by reaction of β-naltrexamine with a fumaroyl chloride alkyl or aralkyl ester. The methyl ester has been named fumarnaltrexamine (FNA).

BRIEF DESCRIPTION OF THE DRAWINGS

The utility of the invention is illustrated in the accompanying drawings in which:

FIG. 1 is a graphic representation of the duration of the inhibitory effect of FNA on morphine analgesia, and FIG. 2 is a graphic representation of the analgesic response of mice to FNA.

DETAILED DESCRIPTION OF THE INVENTION

The design rationale for the opioid receptor alkylating agents is based on the finding that CNA is an irreversible narcotic antagonist in vitro and an ultralong-acting antagonist in vivo [Portoghese et al, supra]. The fact that the alkylating group, $N(CH_2CH_2Cl)_2$ is located in the C-6 position of CNA indicates that there is a nucleophile adjacent to opioid receptors when CNA is reversibly bound to the receptor. Because the high reactivity of $N(CH_2CH_2Cl)_2$ endows CNA with little ability to selectively alkylate one class of opioid receptors over another, the attachment of a less reactive group at either C-6, its equivalent position, or a neighboring position should allow considerably greater selectivity. This would therefore enable one to selectively alkylate one type of opioid receptor in the presence of a variety of other opioid receptors. By virtue of the decreased reactivity and greater selectivity, such ligands also should possess fewer side effects.

This rationale was used in the design of FNA. This new long-acting narcotic antagonist is highly selective and exhibits no toxic effects at a single dose which completely blocks the effects of morphine for at least three days. The selectivity of FNA has been demonstrated in the electrically stimulated guinea pig ileum by its ability to irreversibly block the agonist effects of morphine or enkephalin but not the agonist effects of pentazocine or nalorphine. In contrast, CNA irreversibly blocks the agonist effects of all of these ligands because the $N(CH_2CH_2Cl)_2$ group is less selective due to its broader spectrum of reactivity with different nucleophiles.

FNA can be readily prepared by reaction of β-naltrexamine with a fumaroyl chloride alkyl or aralkyl ester. The ester moiety may be, for example, methyl, ethyl, propyl, butyl, amyl, etc., or $(CH_2)_n$ Ar wherein n=1 to 5 or greater. The Ar substituent may be, for example, phenyl; substituted phenyl wherein the substituent is halogen, hydroxy, nitro, methoxy, methyl, trifluoromethyl, amino, etc.; furane; naphthyl; thiophene and the like. Where R' is allyl or substituted allyl, the starting amine is one containing the allyl or substituted allyl group. In the latter, the substituent may be methyl, ethyl, propyl, halogen, and the like.

Where the Michael acceptor is an acrylamide, the compounds are prepared by reacting β-naltrexamine with the corresponding acid chloride. R may be, for example, acetylacrylamide, acrylamide, α-haloacrylamide in which the halogen is chlorine, iodine or bromine, or the like. Where R is a haloacetamide, β-naltrexamine is condensed with a haloacetoxy-succinimide in which the halogen is iodine, chlorine or bromine. Where R is isothiocyanate, the compound is prepared by reacting β-naltrexamine with thiophosgene.

The compounds may be presented in pharmaceutical preparations prepared by any of the well-known methods of pharmacy, i.e., they may be presented as an acid salt, i.e., HCl salt, sulfate, phosphate, nitrate, methanesulfonate, tartrate, etc. For parenteral administration, the compound may be presented in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants.

For oral administration, fine powders or granules of the compound may contain diluents and dispersing and surface active agents, and may be prepared in a draft in water or in a syrup, in capsules or cachets in the dry state or in a non-aqueous suspension, when a suspending agent may be included; in tablets, when binders and lubricants may be included; or in a suspension in water or a syrup or an oil, or in a water/oil emulsion, when flavoring, preserving, suspending, thickening and emulsifying agents may be included. The granules or the tablets may be coated.

The invention is further illustrated by the following examples:

EXAMPLE I

FNA was synthesized by reaction of 1 mmole of naltrexamine:

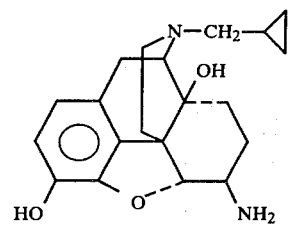

[as the dihydrochloride or diacetate salt in 30 ml tetrahydrofuran-water (2:1) containing $Na_2CO_3$ (0.6 g)]; [Jaing et al, *J. Med. Chem.*, 20, 1100 (1977)] with 1.1 mmole of the monomethyl ester of fumaroyl chloride:

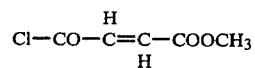

[Acheson et al, *J. Chem. Soc.* 526 (1964)] in 10 ml tetrahydrofuran (THF) at room temperature. The acid chloride was added over 15 minutes and stirring was continued for an additional 30 minutes at about 20° C. After extraction (EtOAc) and removal of solvent, free base FNA was crystallized from $Et_2O$-hexane (yield, 68%); mp 101°–103° C.; EIMS m/e 454 (M+); TLC $R_f$(silica gel; EtOAc-$NH_4OH$, 100:1) 0.54; NMR ($CD_3COCD_3$) C-5 H δ 4.49 (d, $J_{5,6}$=7.6 Hz), vinyls δ 7.03 and 6.82 (J=15.4 Hz). The base FNA was converted to the HCl salt and crystallized from MeOH-$Et_2O$ (1:1), mp>285° C.; $[\alpha]_D$ −164° (c 0.5, MeOH); Anal ($C_{25}H_{31}N_2O_6Cl$) C, H, N.

The utility of the compounds of the present invention is shown by the following:

EXAMPLE II

The duration of the inhibitory effect of FNA on morphine was tested. At 4.8 nmol/mouse (intracebroventricular) or at 5 mg/kg i.p. in the rat, the antagonist effects of FNA (as its HCl salt) lasted at least three days (FIG. 1). The vertical bars represent 95% confidence intervals of the ED50 values. The antagonistic effect of naloxone was tested 2 hours after administration and its effect had already dissipated.

EXAMPLE III

Experiments with the electrically stimulated guinea pig ileal longitudinal muscle indicated that its response to morphine and enkephalin are inhibited irreversibly by incubation with FNA ($2 \times 10^{-8}$ M) for 30 minutes. Similar treatment of the ileum with FNA did not inhibit the agonist effects of nalorphine or pentazocine, thereby illustrating the selectivity of this agent. The results are shown in the table:

| Agonist | IC50 (M × 10⁸) | | Ratio FNA/Control |
| --- | --- | --- | --- |
| | Control | After FNA[a] | |
| Morphine | 2.77 | 16.0 | 5.8 |
| D-Ala²—Met—enkephlin-Amide | 0.42 | 2.91 | 6.9 |
| Nalorphine | 2.81 | 2.52 | 0.9 |

[a]FNA (2 × 10⁻⁸) was incubated with the guinea pig ileal muscle for 30 minutes, washed 20 times, and tested with morphine.

EXAMPLE IV

The analgesic response of mice to FNA was tested. FNA produces a reversible analgesia (FIG. 2) which is not reversed by its own antagonistic properties.

EXAMPLES V–XIV

In vitro biological data for ten additional compounds is shown in the table. All of the compounds showed receptor selectivity similar to FNA. Details of the assay are found in Rang, *Br. J. PHarmacol.*, 22, 356 (1964).

It is apparent that many modifications and variations of this invention as hereinbefore set forth may be made without departing from the spirit and scope thereof. The specific embodiments described are given by way of example only and the invention is limited only by the terms of the appended claims.

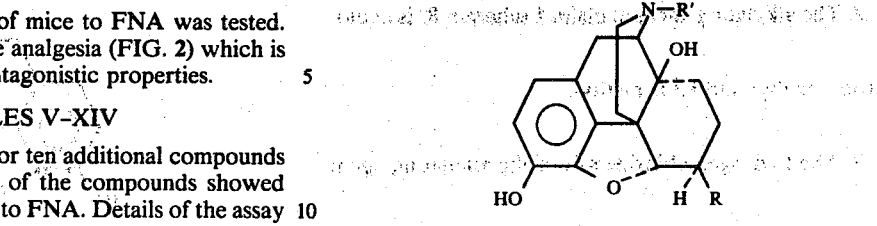

wherein R is an ester having the general formula:

$$NHCOC{=}CCOOR^2$$ 
(with H above and H below)

wherein $R^2$ is $(CH_2)_nH$ or $(CH_2)_nAr$ and n is 1 to 5,

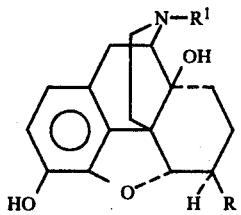

| | R | $R^1$ | $IC_{50}{}^a$ Ratio[b] |
|---|---|---|---|
| (V) | H<br>NHCO—C=C—COOEt<br>H | $CH_2CH(CH_2)_2$ | 2.8 |
| (VI) | H<br>NHCO—C=C—COOPr<br>H | $CH_2CH(CH_2)_2$ | 4.4 |
| (VII) | H<br>NHCO—C=C—COOCH$_2$C$_6$H$_5$<br>H | $CH_2CH(CH_2)_2$ | 3.4 |
| (VIII) | H<br>NHCO—C=C—COO(CH$_2$)$_2$C$_6$H$_5$<br>H | $CH_2CH(CH_2)_2$ | 12.8 |
| (IX) | H<br>NHCO—C=C—COCH$_3$<br>H | $CH_2CH(CH_2)_2$ | 6.4 |
| (X) | NHCO—CH=CH$_2$ | $CH_2CH(CH_2)_2$ | 1.9 |
| (XI) | Cl<br>NHCO—C=CH$_2$ | $CH_2CH(CH_2)_2$ | 8.2 |
| (XII) | NHCO—CH$_2$I | $CH_2CH(CH_2)_2$ | 25.6[c] |
| (XIII) | N=C=S | $CH_2CH(CH_2)_2$ | 2.3 |
| (XIV) | H<br>NHCO—C=C—COOCH$_3$<br>H | $CH_2CH=CH_2$ | 6.4[d] |

[a] The concentration of morphine required to inhibit by 50% the twitch of the electrically stimulated guinea pig ileal longitudinal muscle strip.
[b] The $IC_{50}$ values of morphine before (control) and after (treated) exposure (30 min) of the ileal preparation to the test compound ($2 \times 10^{-8}$ M) followed by 20 washes are expressed as a ratio, morphine $IC_{50}$ (treated)/morphine $IC_{50}$ (control).
[c] concentration of test compound, $10^{-6}$ M.
[d] concentration of test compound, $10^{-7}$ M.

The embodiments of the invention in which an exclusive property or privilege is claimed are defined as follows:

1. A selective opioid receptor alkylating agent having the formula:

wherein Ar is phenyl, furane, naphthyl, thiophene or substituted phenyl, the substituent being halogen, hydroxy, nitro, methoxy, methyl, trifluoromethyl or amino, and R' is selected from the group consisting of cyclopropylmethyl, allyl and substituted allyl, the substituent being methyl, ethyl, propyl or halogen, and pharmaceutically acceptable salts thereof.

2. The alkylating agent of claim 1 wherein R' is cyclopropylmethyl and $R^2$ is methyl.

3. The hydrogen chloride salt of the alkylating agent of claim 2.

4. A selective opioid receptor alkylating agent having the formula:

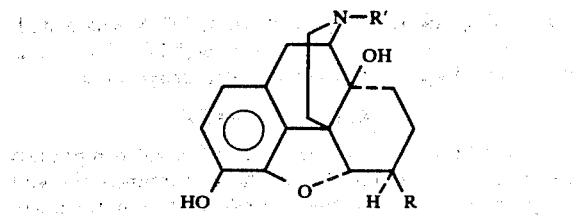

wherein R is isothiocyanate, and R' is selected from the group consisting of cyclopropylmethyl, allyl and substituted allyl, the substituent being methyl, ethyl, propyl or halogen, and pharmaceutically acceptable salts thereof.

UNITED STATES PATENT AND TRADEMARK OFFICE
CERTIFICATE OF CORRECTION

PATENT NO. : 4,362,870
DATED : December 7, 1982
INVENTOR(S) : Philip S. Portoghese It is certified that error appears in the above-identified patent and that said Letters Patent is hereby corrected as shown below:

On the title page, under Abstract, the structural formula should appear as follows:

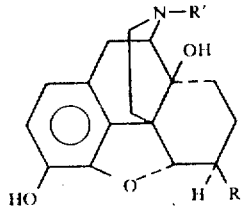

Column 1, line 59, "o" should be --to--.

Signed and Sealed this

Twenty-ninth Day of November 1983

[SEAL]

Attest:

GERALD J. MOSSINGHOFF

Attesting Officer

Commissioner of Patents and Trademarks